United States Patent
Boukhny et al.

[11] Patent Number: 5,645,530
[45] Date of Patent: Jul. 8, 1997

[54] PHACOEMULSIFICATION SLEEVE

[75] Inventors: Mikhail Boukhny, Laguna Beach; Thomas G. Capetan, Corona Del Mar, both of Calif.

[73] Assignee: Alcon Laboratories, Inc., Fort Worth, Tex.

[21] Appl. No.: 494,270

[22] Filed: Aug. 28, 1995

[51] Int. Cl.$^6$ .................................................. A61N 1/30
[52] U.S. Cl. ............................ 604/22; 606/107; 604/175
[58] Field of Search ................................. 138/121, 173; 604/22, 263, 264, 280, 192, 195, 198, 216, 164, 174, 93, 116, 175; 606/107, 108, 162; 222/95, 96

[56] References Cited

U.S. PATENT DOCUMENTS

| | | | |
|---|---|---|---|
| 2,935,067 | 3/1960 | Bouet . | |
| 3,134,380 | 5/1964 | Armao | 605/198 X |
| 3,884,238 | 5/1975 | O'Malley et al. . | |
| 4,296,071 | 10/1981 | Weiss et al. | 604/216 X |
| 4,392,859 | 7/1983 | Dent | 604/198 |
| 4,515,583 | 5/1985 | Sorich . | |
| 4,573,979 | 3/1986 | Blake . | |
| 4,772,276 | 9/1988 | Wiita et al. | 604/283 |
| 4,808,154 | 2/1989 | Freeman . | |
| 4,921,147 | 5/1990 | Poirier | 138/121 |
| 4,994,067 | 2/1991 | Summer . | |
| 5,058,570 | 10/1991 | Idemoto et al. . | |
| 5,071,421 | 12/1991 | Stahl | 606/107 |
| 5,084,009 | 1/1992 | Mackool . | |
| 5,116,326 | 5/1992 | Schmidt | 604/198 |
| 5,188,589 | 2/1993 | Wypych et al. . | |
| 5,211,625 | 5/1993 | Sakurai et al. . | |
| 5,282,786 | 2/1994 | Ureche . | |
| 5,286,256 | 2/1994 | Mackool . | |
| 5,354,265 | 10/1994 | Mackool | 604/22 |
| 5,370,134 | 12/1994 | Chin et al. . | |
| 5,540,699 | 7/1996 | Smith . | |

FOREIGN PATENT DOCUMENTS 0180214  5/1986  European Pat. Off. .

*Primary Examiner*—Mark Bockelman
*Attorney, Agent, or Firm*—Jeffrey S. Schira

[57] ABSTRACT

A phacoemulsification sleeve having a centering ring isolated within an outer shell. A bellows-like sleeve between the handpiece and the outer shell provides a fluid path for the irrigating fluid.

26 Claims, 2 Drawing Sheets

PHACOEMULSIFICATION SLEEVE

BACKGROUND OF THE INVENTION

The present invention relates generally to endoscopic surgical equipment and more specifically to phacoemulsification sleeves.

Phacoemulsification involves emulsifying the natural lens in situ using an ultrasonically vibrating hollow needle. The emulsified lens is aspirated out of the eye through the hollow needle simultaneously with the infusion of a saline solution. The saline solution is generally infused through the space between the outside of the needle and a thin, flexible sleeve that is held coaxial with the needle. One of the primary benefits of phacoemulsification is that the lens can be removed through a very small incision. With the recent introduction of foldable intraocular lenses, and the ability to insert these replacement lenses through even smaller incisions, the desirable size of the incision through which the phacoemulsification tip and irrigating sleeve must pass is also becoming smaller.

While the desirable phacoemulsification indsion size has become smaller, the overall diameter of the cutting tip/sleeve combination has remained relatively constant. As a result, the tip/sleeve combination must be used in a very tight wound. While the elasticity of the eye tissue allows adequate manipulation of the tip/sleeve within the wound, this tight wound structure compresses the sleeve around the vibrating tip, allowing heat to be generated by the vibrating tip rubbing against the sleeve. If the amount of heat generated is excessive, burning of the eye tissue can result. A further concern is that when the sleeve is compressed around the cutting tip, the irrigation fluid path between the tip and the sleeve is restricted, thereby reducing the flow of the cooling irrigation fluid.

There have been numerous attempts in the past to prevent the sleeve from being collapsed around the cutting tip. For example, U.S. Pat. Nos. 5,084,009, 5,286,256, 5,354,265 (Mackool) and 5,282,786 (Ureche) describe infusion sleeves having a flexible component and a rigid component. The flexible component allows the cutting tip to be manipulated within the eye while the rigid component helps prevent the sleeves from being collapsed around the cutting tip. U.S. Pat. Nos. 4,808,154 (Freeman) and 5,188,589 (Wypych) describe sleeves having grooves or other texturing within the sleeve that allows irrigating solution to flow through the tip even when the sleeve is collapsed around the cutting tip.

While these prior art devices can reduce the amount of friction generated heat, all of these devices allow the cutting tip to contact the sleeve, particularly as the size of wound is decreased. Thus, heat can still be transmitted to the ocular tissue. Accordingly, a need continues to exist for a device that more effectively insulates the cutting tip from ocular tissue.

BRIEF SUMMARY OF THE INVENTION

The present invention improves upon prior art infusion sleeves by providing a sleeve having a centering ring isolated within an outer shell. The outer shell prevents the incision from collapsing around the cutting tip and the centering ring prevents the cutting tip from contacting the outer shell while still allowing the cutting tip to be manipulated by the surgeon. A bellows-like sleeve between the handpiece and the outer shell provides a fluid path for the irrigating fluid. As a result, frictional heating of the wound tissue is reduced substantially and the flow of cooling irrigation fluid is maintained.

Accordingly, one objective of the present invention is to provide an infusion sleeve having an outer shell that prevents the incision tissue from collapsing around the cutting tip.

Another objective of the present invention is to provide an infusion sleeve having a centering ring for the cutting tip.

Yet another objective of the present invention is to provide an infusion sleeve that allows the cutting tip to be manipulated without contacting the wound tissue.

These and other advantages and objectives of the present invention will become apparent from the detailed description, drawings and claims that follow.

DETAILED DESCRIPTION OF THE INVENTION

Figure 1:
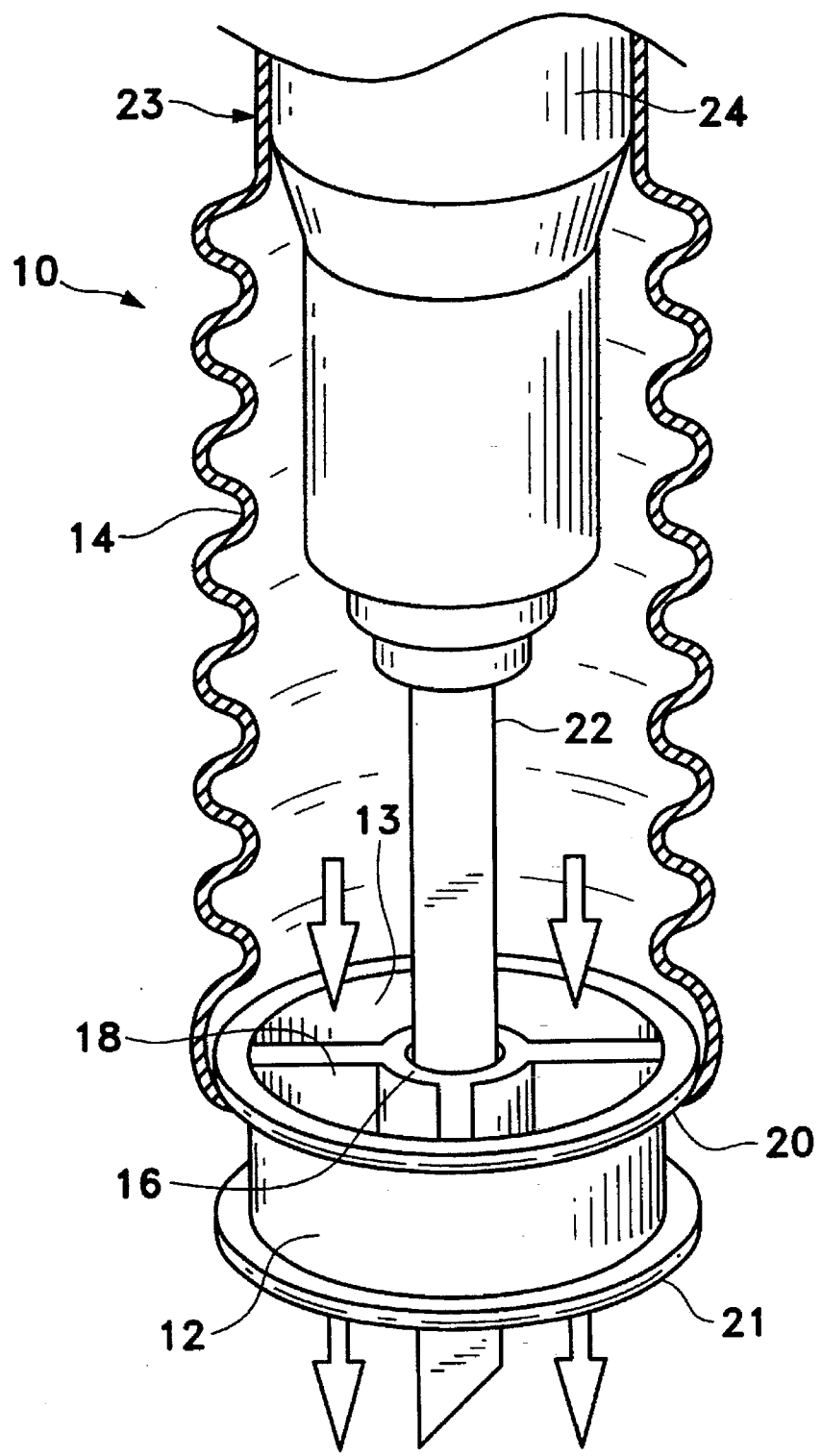
FIG. 1 is an exploded partial cross-sectional view of one embodiment of the present invention.

As can be seen in FIG. 1, the first embodiment 10 of the present invention consists primarily of rigid sleeve 12 and flexible irrigation bellows 14. Rigid sleeve 12 is preferably made out of titanium or stainless steel, but other suitably rigid materials, such as composite material well-known in the art may also be used. Sleeve 12 contains flanges 20 and 21 and centering ring 16 held within bore 13 of sleeve 12 by web-like plates 18. Ring 16 centers cutting tip 22 within sleeve 12 during use and isolates cutting tip 22 from the wound tissue. Flange 20 provides a connection point for bellows 14 and prevents sleeve 12 from being inserted too far into the wound, and flanges 20 and 21 help prevent sleeve 12 from becoming dislodged during use. Sleeve 12, ring 16, flanges 20 and plates 18 preferably are formed as a single piece. Sleeve 12 preferably is elliptical or round or any similar geometric shape that best conforms to the shape of the incision. By way of example, round sleeve 12 has an outer diameter of between 0.04 inches and 0.2 inches, an inner diameter of between 0.02 inches and 0.199 inches and a wall thickness of between 0.0001 inches and 0.01 inches. Ring 16 preferably has an outer diameter of between 0.0101 inches and 0.151 inches, an inner diameter of between 0.01 inches and 0.15 inches and a wall thickness of between 0.0001 inches and 0.01 inches. Plates 18 preferably have a thickness of between 0.0001 inches and 0.01 inches.

Bellows 14 attaches between body 23 of handpiece 24 and flange 20 on sleeve 12. Alternatively, bellows 14 and sleeve 12 may be molded in one-piece, eliminating the need for flange 20. In an additional embodiment (not shown) flanges 20 and 21 can be formed as part of bellows 14, and bellows 14 will extend over the entire length of sleeve 12. Bellows 14 preferably is made from a thin-walled, flexible material such as silicone rubber or metal. Bellows 14 provides an irrigation fluid path between handpiece 24 and sleeve 12 and, because of its flexible nature, bellows 14 can act as a fluid capacitance chamber to help reduce fluid pressure spikes during surgery.

Figure 2:
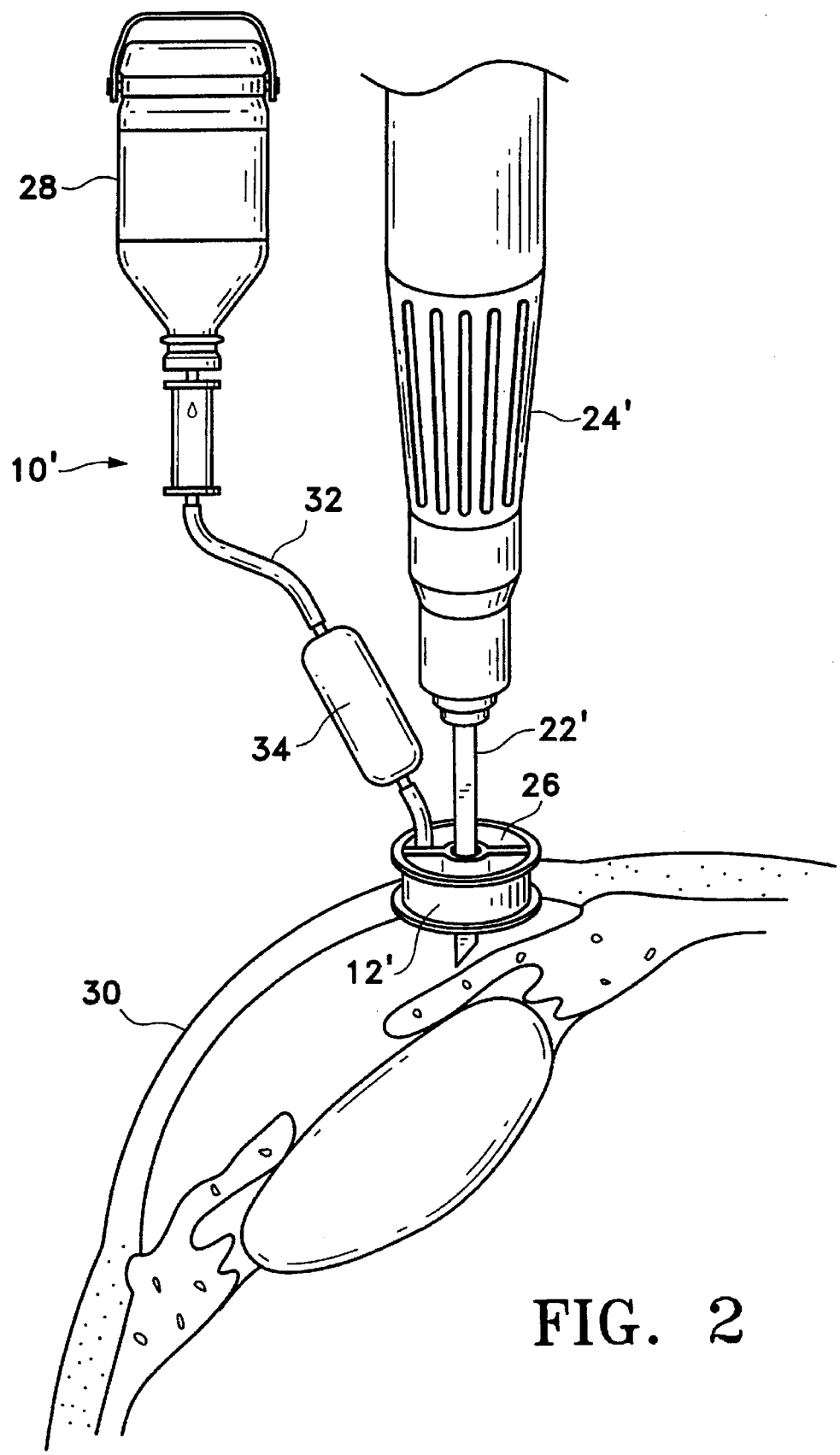
FIG. 2 is a perspective view of a second embodiment of the present invention.

As best seen in FIG. 2, in second embodiment 10' of the present invention, sleeve 12' is used without bellows 14. Instead, the outer side of sleeve 12' is sealed fluid tight by compliant member 26. Compliant member 26 preferably is made from silicone rubber and is integrally molded with sleeve 12'. In use, cutting tip 22' is inserted through sleeve 12', piercing compliant member 26, which forms a fluidfight seal around cutting tip 22'. Infusion fluid from fluid source 28 is provided to eye 30 through separate infusion line 32, which is inserted through compliant member 26 is a manner similar to cutting tip 22'. Infusion line 32 may contain a compliance chamber 34 that acts in a manner similar to bellows 14 of the first embodiment to help reduce fluid pressure spikes during surgery.

This description is given for purposes of illustration and explanation. It will be apparent to those skilled in the relevant art that modifications may be made to the invention as herein described without departing from its scope or spirit.

We claim:

1. A phacoemulsification sleeve, comprising:
   i) a rigid sleeve having a bore, an outwardly extending ring held within the bore and a flange on an end of said sleeve for preventing the sleeve from being dislodged from a phacoemulsification incision when inserted therein, the rigid sleeve being sized and shaped to fit within a phacoemulsification incision; and
   ii) a flexible irrigation bellows connected to the rigid sleeve forming an irrigation fluid path, the irrigation fluid path extending through the sleeve and into the phacoemulsification incision when said sleeve is inserted into a phacoemulsification incision.

2. The phacoemulsification sleeve of claim 1 wherein the ring is centered within the sleeve.

3. The phacoemulsification sleeve of claim 1 wherein the rigid sleeve and ring are formed as a single piece.

4. The phacoemulsification sleeve of claim 3 wherein the rigid sleeve and the ring comprise stainless steel.

5. The phacoemulsification sleeve of claim 3 wherein the rigid sleeve and the ring comprise titanium.

6. The phacoemulsification sleeve of claim 1 wherein the flexible irrigation bellows comprises silicone rubber.

7. The phacoemulsification sleeve of claim 1 wherein the rigid sleeve is elliptical.

8. A phacoemulsification handpiece comprising:
   i) a body having ultrasonic vibration means;
   ii) a vibrating phacoemulsification cutting tip connected to the body and extending from the handpiece;
   iii) a rigid sleeve having a bore and a ring held within the bore positioned so that the cutting tip passes through the ring; and
   iv) a flexible irrigation bellows having two ends connected to the rigid sleeve on a first end and to the body on a second end, the bellows forming an irrigation fluid path around the cutting tip and through the rigid sleeve.

9. The phacoemulsification handpiece of claim 8 wherein the ring is centered within the sleeve.

10. The phacoemulsification handpiece of claim 8 wherein the rigid sleeve and ring are formed as a single piece.

11. The phacoemulsification handpiece of claim 10 wherein the rigid sleeve and the ring comprise stainless steel.

12. The phacoemulsification handpiece of claim 10 wherein the rigid sleeve and the ring comprise titanium.

13. The phacoemulsification handpiece of claim 8 wherein the flexible irrigation bellows comprises silicone rubber.

14. The phacoemulsification handpiece of claim 8 wherein the rigid sleeve is elliptical.

15. A phacoemulsification sleeve comprising:
    i) a rigid, elliptical sleeve having a bore and a ring held within the bore by at least two inwardly extending plates, the rigid sleeve and ring formed as a single piece, the rigid sleeve being sized and shaped to fit within a phacoemulsification incision; and
    ii) a flexible irrigation bellows connected to the rigid sleeve forming an irrigation fluid path, the irrigation fluid path extending through the sleeve and into the phacoemulsification incision when said sleeve is inserted into a phacoemulsification incision.

16. The phacoemulsification sleeve of claim 15 wherein the ring is centered within the sleeve.

17. The phacoemulsification sleeve of claim 15 wherein the rigid sleeve and the ring comprise stainless steel.

18. The phacoemulsification sleeve of claim 15 wherein the rigid sleeve and the ring comprise titanium.

19. The phacoemulsification sleeve of claim 15 wherein the flexible irrigation bellows comprises silicone rubber.

20. A phacoemulsification sleeve comprising:
    i) a rigid sleeve having, an outer side, a bore and a ring held spaced from said rigid sleeve within the bore, the rigid sleeve being sized and shaped to fit within a phacoemulsification incision;
    ii) a compliant member attached to the outer side of the rigid sleeve so as to form a fluid tight seal across the bore; and
    iii) a means for providing irrigation fluid through the compliant member extending through said compliant member between the ring and the sleeve.

21. The phacoemulsification sleeve of claim 20 wherein the ring is centered within the sleeve.

22. The phacoemulsification sleeve of claim 20 wherein the rigid sleeve and ring are formed as a single piece.

23. The phacoemulsification sleeve of claim 22 wherein the rigid sleeve and the ring comprise stainless steel.

24. The phacoemulsification sleeve of claim 22 wherein the rigid sleeve and the ring comprise titanium.

25. The phacoemulsification sleeve of claim 20 wherein the compliant member comprises silicone rubber.

26. The phacoemulsification sleeve of claim 20 wherein the rigid sleeve is elliptical.

* * * * *